United States Patent [19]

Odorisio et al.

[11] Patent Number: 5,244,953
[45] Date of Patent: Sep. 14, 1993

[54] SUBSTITUTED 1-AMINONAPHTHALENES AND STABILIZED COMPOSITIONS

[75] Inventors: Paul A. Odorisio, Edgewater; David E. Chasen, Teaneck, both of N.J.; Stephen D. Pastor, Danbury, Conn.

[73] Assignee: Ciba-Geigy Corporation, Ardsley, N.Y.

[21] Appl. No.: 928,254

[22] Filed: Aug. 10, 1992

Related U.S. Application Data

[62] Division of Ser. No. 697,123, May 7, 1991, Pat. No. 5,160,647.

[51] Int. Cl.⁵ .............................................. C08K 5/18
[52] U.S. Cl. .................................................. 524/256
[58] Field of Search ...................................... 524/256

[56] References Cited

U.S. PATENT DOCUMENTS

| | | |
|---|---|---|
| 1,890,916 | 12/1932 | Semon . |
| 3,244,517 | 4/1966 | Lind . |
| 3,414,618 | 12/1968 | Randall . |
| 3,598,592 | 8/1971 | Cescon . |
| 3,634,248 | 1/1972 | Andreas, Jr. . |
| 3,849,322 | 11/1974 | Wendler et al. . |
| 3,944,492 | 3/1976 | Wheeler . |
| 4,426,475 | 1/1984 | Brassat et al. . |
| 4,440,657 | 4/1984 | Metro et al. . |

FOREIGN PATENT DOCUMENTS

| | | |
|---|---|---|
| 1123103 | 2/1962 | Fed. Rep. of Germany . |
| 1517301 | 7/1968 | France . |
| 162897 | 2/1934 | Switzerland . |

OTHER PUBLICATIONS

C. A. vol. 40. 4728 (1946), Comptes Rendus Hebomadaires Des Seances De L'Academie Des Sciences p. 665–666.
Journal of Organic Chemistry vol. 29, 1964 pp. 967–968.
J. E. Kuder, et al., J. Org. Chem. 44, 761(1979).
M. M. Sprung, Chem. Rev. 26, 297(1940).
E. C. Wagner, J. Org. Chem. 19, 1862(1954).
A. R. Katrisky et al., Synthesis, 1990, 341.

*Primary Examiner*—Veronica P. Hoke
*Attorney, Agent, or Firm*—Luther A. R. Hall

[57] ABSTRACT

Substituted 1-aminonaphthalenes of formula I

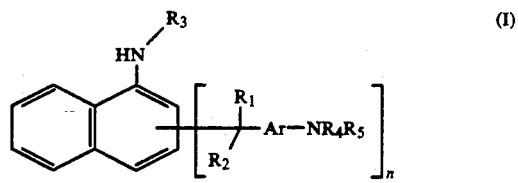

wherein n is 1–3, Ar is arylene, $R_1$ and $R_2$ are independently hydrogen, alkyl or phenyl, $R_3$ is hydrogen, alkyl or substituted alkyl, and $R_4$ and $R_5$ have independently the same definitions as $R_3$ or are independently aryl, substituted aryl or cycloalkyl, are effective stabilizers for lubricating oil or polymer compositions. The instant compounds are particularly effective in lubricating oil compositions when used with a diarylamine antioxidant.

6 Claims, No Drawings

SUBSTITUTED 1-AMINONAPHTHALENES AND STABILIZED COMPOSITIONS

This is a divisional of Ser. No. 697,123 filed May 7, 1991 now U.S. Pat. No. 5,160,647.

The instant invention pertains to novel substituted 1-aminonaphthalenes and to lubricating oil or polymer compositions stabilized by said compounds. Lubricating oil compositions are particularly well stabilized when they contain the novel substituted 1-aminonaphthalenes in combination with a diarylamine antioxidant.

BACKGROUND OF THE INVENTION

U.S. Pat. No. 3,634,248 describes the products of reaction between an aromatic amine and an aldehyde carried out from about 75° C. to about 300° C. The products described consist of two amino groups linked through an alkylidene radical derived from the aldehyde, such as:

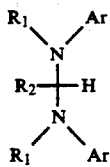

U.S. Pat. No. 3,244,517 describes an electrophotographic process in which the photoconductor is a resinous condensation product of a saturated aldehyde and an aromatic amine.

U.S. Pat. No. 3,598,592 describes aminotriarylmethane compounds which are substituted on the aryl groups by dialkylamino or dibenzylamino groups. These compounds are tertiary amines unlike the instant compounds which are substituted on the aryl groups only by secondary amino moieties.

The instant compounds of this invention are structurally different from the materials described in these patents.

Similar triphenylmethane derivatives substituted on the aryl group by tertiary amino groups are described by J. E. Kuder et al., J. Org. Chem. 44, 761 (1979). The instant compounds differ from those disclosed by Kuder et al.

Condensation reactions of aromatic amines and aldehydes have been the subject of many academic studies. For a review of the earlier literature see M. M. Sprung, Chem. Rev., 26, 297 (1940).

For more recent reviews see E. C. Wagner, J. Org. Chem., 19, 1862 (1954) and A. R. Katrizky et al., Synthesis, 341 (1990).

No mention of the instant compounds is made in these reports.

OBJECTS OF THE INVENTION

One object of the instant invention is to provide new substituted 1-aminonaphthalene compounds which are useful as stabilizers for lubricating oil compositions.

Another object of the instant invention is to provide lubricating oil compositions stabilized against oxidation, sludge, varnish, coke and deposit formation and viscosity increases by the presence of an effective stabilizing amount of a substituted 1-aminonaphthalene compound of this invention.

Another object of the instant invention is to provide polymer compositions stabilized against thermal and oxidative degradation by the presence of an effective stabilizing amount of a substituted 1-aminonaphthalene compound of this invention.

DETAILED DISCLOSURE

The compounds of this invention report impart superior stabilization to lubricating oils, particularly to synthetic ester lubricating oils, during high temperature operation in a turbine aircraft engine.

Novel substituted 1-aminonaphthalene compositions comprise a lubricating oil, an optional diarylamine antioxidant, and a substituted 1-aminonaphthalene of formula (I).

The instant invention pertains to a compound of formula I

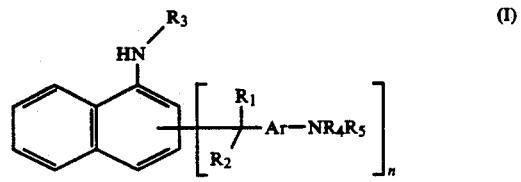

wherein n is 1, 2 or 3,

Ar is an arylene group of 6 to 14 carbon atoms which is substituted by $-NR_4R_5$, $R_3$, $R_4$ and $R_5$ are independently hydrogen, a straight or branched chain alkyl of 1 to 18 carbon atoms, said alkyl group independently terminated with an aryl group, with a substituted aryl group, with an alkenyl group of 3 to 6 carbon atoms, with $-OR_6$, with $-NR_7R_8$, with $-SR_9$, with $-CO_2R_{10}$, or with $-CONR_{11}R_{12}$ wherein $R_6$, $R_7$, $R_8$, $R_9$, $R_{10}$, $R_{11}$, and $R_{12}$ are independently hydrogen or an alkyl group of 1 to 18 carbon atoms, or the aforementioned alkyl group is independently interrupted by an arylene group of 6 to 10 carbon atoms, by said arylene substituted by one or two alkyl groups of 1 to 8 carbon atoms, by $-O-$, by $-S-$, by $-SO-$, by $-SO_2-$, by $-CO-$, by $-CO_2-$, by $-CONR_{13}-$ or by $-NR_{14}-$ wherein $R_{13}$ and $R_{14}$ independently have the same definition as $R_6$; or $R_3$, $R_4$ and $R_5$ are independently an aryl group of 6 to 14 carbon atoms, said aryl group independently substituted by one, two or three alkyl groups of 1 to 18 carbon atoms, by $-CF_3$ or by $-CO_2R_{15}$ wherein $R_{15}$ has the same definition as $R_6$; or $R_3$, $R_4$ and $R_5$ are independently phenyl substituted by the group

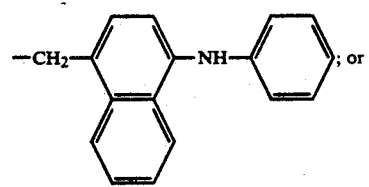

$R_3$, $R_4$ and $R_5$ are independently a cycloalkyl group having 5 to 12 carbon atoms; and $R_1$ and $R_2$ are independently hydrogen, a straight or branched chain alkyl of 1 to 18 carbon atoms, phenyl or 2-furyl;

with the proviso that at least one of $R_4$ and $R_5$ is always hydrogen.

Preferably, the compound of formula I is one where
n is 1,
Ar is an arylene group of 6 to 10 carbon atoms which is substituted by $NR_4R_5$,
$R_4$ and $R_5$ are independently hydrogen, a straight or branched chain alkyl of 1 to 18 carbon atoms, an aryl group of 6 to 10 carbon atoms or said aryl group substituted by one or two alkyl groups of 1 to 18 carbon atoms,
$R_1$ and $R_2$ are independently hydrogen or a straight or branched chain alkyl of 1 to 7 carbon atoms, and
$R_3$ is a straight or branched chain alkyl of 1 to 18 carbon atoms, an aryl group of 6 to 10 carbon atoms or said aryl group substituted by one or two alkyl groups of 1 to 18 carbon atoms.

Most preferably the compounds of formula I are those where
$R_1$ is hydrogen;
$R_2$ is hydrogen or alkyl of 1 to 7 carbon atoms;
$R_3$ is alkyl of 1 to 8 carbon atoms, phenyl or phenyl substituted by one alkyl of 4 to 12 carbon atoms;
Ar is phenylene or naphthylene,
$R_4$ is hydrogen; and
$R_5$ is alkyl of 1 to 8 carbon atoms, phenyl or phenyl substituted by one alkyl of 4 to 12 carbon atoms.

The instant invention also pertains to a lubricating oil composition stabilized against oxidative and thermal degradation which comprises
(a) a lubricating oil subject to thermal or oxidative degradation, and
(b) an effective stabilizing amount of a compound of formula I.

Preferably the lubricating oil is a synthetic ester lubricating oil.

The instant invention also pertains to said lubricating oil composition which additionally contains (c) an effective stabilizing amount of a diarylamine, preferably N,N-di(4-tert-octylphenyl)amine, diphenylamine, N-phenyl-1-naphthylamine, N-(4-tert-octylphenyl)-2-naphthylamine, reaction product of N-phenylbenzylamine and 2,2,4-trimethylpentene, reaction product of diphenylamine and 2,2,4-trimethylpentene, reaction product of N-phenyl-1-naphthylamine and 2,2,4-trimethylpentene, phenothiazine, 3,7-di-tert-octylphenothiazine, N-phenyl-2-naphthylamine, 4-tert-octyldiphenylamine, 4-isopropoxydiphenylamine, 4-n-butoxydiphenylamine, 4-n-octoxydiphenylamine, 4-n-decoxydiphenylamine, 4-n-dodecoxydiphenylamine, diphenyl-p-phenylenediamine, 4-n-hexadecoxydiphenylamine, 4-(3,5,5-trimethylhexoxy)diphenylamine, 4-n-octoxyphenyl-2-naphthylamine, 4,4'-di-n-decoxydiphenylamine, 2,5-dimethoxy-4'-n-octoxydiphenylamine, 3-n-hexadecoxydiphenylamine or 4-n-decoxyphenyl-2-naphthylamine.

The instant invention also pertains to said lubricating oil composition which additionally contains (d) an effective stabilizing amount of a phenolic antioxidant, preferably 2,6-di-tert-butylphenol, 2,6-di-tert-butyl-4-methylphenol, methyl 3,5-di-tert-butyl-4-hydroxyhydrocinnamate, isooctyl 3,5-di-tert-butyl-4-hydroxyhydrocinnamite, n-octadecyl 3,5-di-tert-butyl-4-hydroxyhydrocinnamate, 4,4'-methylene-bis(2,6-di-tert-butylphenol), 2,2'-thio-bis(6-tert-butyl-4-methylphenol), neopentanetetrayl tetrakis(3,5-di-tert-butyl-4-hydroxyhydrocinnamate), 1,3,5-tris(3,5-tris(3,5-di-tert-butyl-4-hydroxybenzyl) isocyanurate and 2,2'-ethylidenebis(4,6-di-tert-butylphenol).

The instant compounds are sufficiently soluble in lubricants to afford the desired stabilizing effects. Suitable concentrations range from about 0.001% to about 10% by weight based on the total lubricant compositions. Preferably the effective stabilizing amount of the instant compounds is from about 0.1% to about 5% by weight of the total lubricant compositions.

The effective stabilizing amount of the diarylamines of component (c) or of the phenolic antioxidants of component (d) is from 0.1 to 10% by weight of the lubricant composition, preferably from 0.5 to 5% by weight.

When Ar is arylene, it is, for example, phenylene, naphthylene, anthracenylene or phenanthrenylene. When any of $R_1$, $R_2$, $R_3$, $R_4$ or $R_5$ is alkyl, it is, for example, methyl, ethyl, isopropyl, n-butyl, sec-butyl, isobutyl, tert-butyl, tert-amyl, 2-ethylhexyl, n-octyl, tert-octyl, lauryl or n-octadecyl; when any of said radicals are cycloalkyl, they are, for example, cyclopentyl, cyclohexyl, cyclooctyl or cyclododecyl; when said radicals are aryl or substituted aryl, they are, for example, phenyl, naphthyl, tolyl, xylyl, 4-tert-octylphenyl, 4-tert-octyl-1-naphthyl, 2,4-di-tert-butylphenyl or 4-tert-dodecylphenyl.

The instant compounds are made by the general procedure of reacting a substituted 1-aminonaphthalene with an aldehyde, preferably formaldehyde, under acidic conditions.

The lubricant which can be stabilized by the instant compounds may be an oil or a grease based on mineral or synthetic oils, these lubricants being well known to those skilled in the art. The term mineral oil includes all mineral oils used for lubricant purposes, such as hydrocarbon mineral oils. The synthetic oil may be, for instance, an aliphatic or aromatic carboxylic ester, a polymeric ester, a polyalkylene oxide, a phosphoric acid ester, polybutenes, alkyl benzenes poly-alpha-olefins or a silicone. Greases may be obtainable from these by adding metal soaps or similar thickeners.

Synthetic ester lubricating oils are preferred and may include diesters and "simple esters, complex esters and polyesters" as those terms are defined in the recitation spanning column 3, line 45 through column 5, line 14 of U.S. Pat. No. 4,440,657, the entire disclosure of which is incorporated here by reference. Carboxylic acid diesters have the formula $T_1$—OCC—alkylene—$COOT_2$ wherein "alkylene" denotes an alkylene residue having from 2 to 14 carbon atoms and $T_1$ and $T_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

When the instant compounds are utilized in a turbo lubricating oil, the basestock typically comprises one or more esters prepared by reacting neo alcohols (such as neopentyl glycol, trimethylolpropane, pentaerythritol) with normal and iso acids having 5 to 10 carbon atoms.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants. For synthetic ester lubricating oils, hydrolysis stabilizers may also be included to form a fully formulated oil.

Examples of Phenolic Antioxidants

1. Alkylated Monophenols 2,6-Di-tert-butyl-4-methylphenol, 2,6-di-tert-butyl-phenol, 2-tert-butyl-4,6-dimethylphenol, 2,6-di-tert-butyl-4-ethyl-phenol, 2,6-di-tert-butyl-4-n-butyl-phenol, 2,6-di-tert-butyl-4-i-butylphenol, 2,6-dicyclopentyl-4-methylphenol, 2-(β-methylcyclohexyl)-4,6-dimethylphenol, 2,6-di-octa-decyl-4-methyl-phenol, 2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methyl-phenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexyl-phenol), 2,2'-methylene-bis-(6-nonyl-4-methyl-phenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonyl-phenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methyl-phenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-Tert-Butyl-4-Hydroxyphenyl)-Propionic Acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-Tert-Butyl-4-Hydroxy-3-Methylphenyl)-Propionic Acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-Tert-Butyl-4-Hydroxyphenyl)-Propionic Acid for example N,N'-Bis-(3,5-di-tert-butyl-4-hydroxy-phenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of Amine Antioxidants

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-aminophenol, di-(4-methoxy-phenyl)-amine, 2,6-di-tert-butyl-4-dimethyl-amino-methyl-phenol, 2,4'-diaminodiphenylmethane, 4,4'-diaminodiphenyl-methane, N,N,N',N'-tetramethyl-4,4'-diamino-diphenylmethane, 1,2-di-(phenylamino)-ethane, 1,2-di-[2-methylphenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine, tert-octylated phenothiazine, 3,7-di-tert-octylphenothiazine.

Examples for Other Antioxidants

Aliphatic or aromatic phosphites, esters of thiodipropionic acid or of thiodiacetic acid, or salts of dithiocarbamic or dithiophosphoric acid.

Examples of Metal Passivators, for Example for Copper, are

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

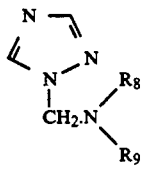

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of Rust Inhibitors are a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y—NH_3—R_{10}CO_2—$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y—NH_2$ with an acid $R_{10}CO_2H$, as disclosed in DE-OS 3437 876 (German Offenlegungsschrift).

g) Compounds having the formula $$R_{12}—X_2—CH_2—CH(OH)—CH_2NR_{13}R_{14}$$

in which $X_2$ is —O—, —S—, —SO_2—C(O)—O— or —N(Rd) in which $R_{12}$ is H or $C_1$–$C_{12}$alkyl, $R_{13}$ is unsubstituted $C_1$–$C_4$alkyl or $C_2$–$C_5$alkyl substituted by one to three hydroxyl groups, $R_{14}$ is hydrogen, unsubstituted $C_1$–$C_4$alkyl or $C_2$–$C_5$alkyl substituted by one to three hydroxyl groups provided that at least one of $R_{13}$ and $R_{14}$ is hydroxy-substituted, and $R_{12}$ is $C_2$–$C_{20}$alkyl —$CH_2$—$CH(OH)$—$CH_2NR_{13}R_{14}$ or $R_{12}$ is $C_2$–$C_{18}$alkenyl, $C_2$–$C_3$alkynyl or $C_5$–$C_{12}$cycloalkyl provided that, when $X_2$ is —O— or —C(O)—O—, $R_{12}$ is branched $C_4$–$C_{20}$alkyl. These compounds are described in GB Patent Specification 2172284A.

h) Compounds having the formula:

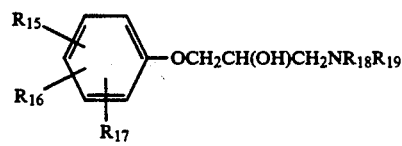

in which $R_{15}$, $R_{16}$, $R_{17}$ are, independently, hydrogen, $C_1$–$C_{15}$alkyl, $C_5$–$C_{12}$cycloalkyl, $C_6$–$C_{15}$aryl or $C_7$–$C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not simultaneously hydrogen and $R_{17}$ is not pentyl. These compounds are described in EP Patent specification 0 252 007.

Examples of Viscosity-Index Improvers are

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of Pour-Point Depressants are

Polymethacrylates, alkylated naphthalene derivatives.

Examples of Dispersants/Detergents are

Polybutenylsuccinic acid-amides or -imides, polybutenyl-phosphonic acid derivatives, basic magnesium-, calcium-, and bariumsulfonates and -phenolates.

Examples of Anti-wear Additives and Extreme Pressure Additives are

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The instant compounds are also useful stabilizers for polymers especially elastomers, such as the crosslinked blends of polypropylene and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene-/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated Monophenols, for Example, 2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated Hydroquinones, for Example, 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated Thiodiphenyl Ethers, for Example, 2,2'-thio-bis-(4-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-Bisphenols, for Example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl Compounds, for Example 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for Example, 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of
β-(3,5-Di-Tert-Butyl-4-Hydroxyphenyl)-Propionic Acid with Monohydric or Polyhydric Alcohols, for Example,

| methanol | diethylene glycol |
| octadecanol | triethylene glycol |
| 1,6-hexanediol | pentaerythritol |

-continued

| | |
|---|---|
| neopentyl glycol | tris-hydroxyethyl isocyanurate |
| thiodiethylene glycol | di-hydroxyethyl oxalic acid diamide |

1.8. Esters of β-(5-Tert-Butyl-4-Hydroxy-3-Methylphenyl)-Propionic Acid with Monohydric or Polyhydric Alcohols, for Example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-Di-Tert-Butyl-4-Hydroxyphenyl)-Propionic Acid for Example, N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine

1.10 Diarylamines, for example, diphenylamine, N-phenyl-1-naphthylamine, N-(4-tert-octylphenyl)-1-naphthylamine, 4,4'-di-tert-octyldiphenylamine, reaction product of N-phenylbenzylamine and 2,4,4-trimethylpentene, reaction product of diphenylamine and 2,4,4-trimethylpentene, reaction product of N-phenyl-1-naphthylamine, 2,4,4-trimethylpentene, phenothiazine, 3,7-di-tert-octylphenothiazine, N-phenyl-2-naphthylamine, 4-tert-octyldiphenylamine, 4-isopropoxy-diphenylamine, 4-n-butoxydiphenylamine, 4-n-octoxydiphenylamine, 4-n-decoxydiphenylamine, 4-n-dodecoxydiphenylamine, diphenyl-p-phenylenediamine, 4-n-hexadecoxydiphenylamine, 4-(3,5,5-trimethylhexoxy)diphenylamine, 4-n-octoxyphenyl-2-naphthylamine, 4,4'-di-n-decoxydiphenylamine, 2,5-dimethoxy-4'-n-octoxydiphenylamine, 3-n-hexadecoxydiphenylamine and 4-n-decoxyphenyl-2-naphthylamine.

1.11 2-Mercaptobenzimidazoles, for Example, 2-mercaptobenzimidazole, 2-mercaptotoluimidazole, zinc salt of 2-mercaptobenzimidazole, zinc salt of 2-mercaptotoluimidazole.

2. UV Absorbers and Light Stabilizers

2.1. 2-(2'-Hydroxyphenyl)-Benzotriazoles for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of Optionally Substituted Benzoic Acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic Acid Diamides for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-Triazines for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal Deactivators for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and Phosphonites for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds Which Destroy Peroxide for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide Stabilizers for example copper salts in combination with iodides and/or phosphorus compounds and salts of divalent manganese.

9. Basic Co-Stabilizers for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating Agents for example, 4-tert-butyl-benzoic acid, adipic acid, diphenylacetic acid.

11. Fillers and Reinforcing Agents for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate[, octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetra-methylpiperidine) and 1,2-dibromoethane, tetrakis(2,2,6,6-tetramethylpiperidin-4-yl) 1,2,3,4-butanetetracarboxylate, tetrakis(1,2,2,6,6- pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/$\beta,\beta,\beta',\beta'$-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/$\beta,\beta,\beta',\beta'$-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate) and 4,4'-ethylenebis(2,2,6,6-tetramethylpiperazin-3-one).

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazin-2-yl]-1,10-diamino-4,7-diazadecane.

The following examples are presented for the purpose of illustration only and are not to be construed to limit the nature of scope of the instant invention in any manner whatsoever.

EXAMPLE 1

4,4'-Methylene-bis[N-(4-tert-octylphenyl)-1-naphthylamine]

Into a suspension of 33.1 g (0.1 mol) of N-(4-tert-octylphenyl)-1-naphthylamine in 150 mL of methanol at ambient temperature is added dropwise 5.5 mL (0.1 mol) of concentrated sulfuric acid. Into the resultant mixture is then added dropwise 4.0 g (0.05 mol) of a 37.6% aqueous solution of formaldehyde. After the addition is complete, the reaction mixture is heated under reflux for 2 hours. After cooling to ambient temperature, the reaction solvent is decanted from the precipitated reaction mass. The precipitated reaction mass is then redissolved into 200 mL of ether and is washed sequentially with 40 mL of a 10% aqueous solution of sodium hydroxide then 50 mL of brine. The organic layer is then dried over anhydrous sodium sulfate and the filtrate is concentrated in vacuo to give 35 g of a reaction residue. The residue is purified by chromatography, using silica gel and a mixture of 95% hexane and 5% ethyl acetate (by volume) as an eluent, to give 22.1 g (65% yield) of the title compound as an off-white solid melting at 80° C.

Analysis

Calcd. for $C_{49}H_{58}N_2$: C, 87.2; H, 8.7; N, 4.1. Found: C, 87.5; H, 8.9; N, 4.0.

EXAMPLE 2

4,4'-Methylene-bis[N-phenyl-1-naphthylamine]

The procedure of Example 1 is repeated using 21.93 g (0.1 mol) of N-phenyl-1-naphthylamine, 4.0 g (0.05 mol) of a 37.6% aqueous solution of formaldehyde and 1.0 mL of concentrated sulfuric acid in 150 mL of methanol to give 24 g of a pink residue. The residue is purified by crystallization from 25 mL of acetonitrile to give 5.4 g (24% yield) of the title compound as an off-white solid melting at 154°-157° C.

Analysis

Calcd.for $C_{33}H_{26}N_2$: C, 88.0; H, 5.8; N, 6.2. Found: C, 87.7; H, 5.9; N, 5.9.

EXAMPLE 3

Condensation Product Mixture of N-Phenyl-1-naphthylamine and Formaldehyde

The procedure of Example 1 is repeated using 43.9 g (0.2 mol) of N-phenyl-1-naphthylamine, 8.0 g (0.1 mol) of a 37.6% aqueous solution of formaldehyde and 2 mL of concentrated sulfuric acid in 300 mL of methanol to give 43.1 g (96% yield) of a pink solid melting at 140° C.

HPLC Analysis

|  | Wt % |
|---|---|
| Unreacted N-phenyl-1-naphthylamine | 13 |
| 4,4'-Methylene-bis[N-phenyl-1-naphthylamine] (Compound of Example 2) | 64 |
| *Higher molecular weight oligomers | balance |

*The balance of the reaction mixture contains higher molecular weight homologs of 4,4'-methylene-bis[N-phenyl-1-naphthylamine].

Compounds having molecular weights of 681, 912 and 1143 are identified by mass spectroscopy. These are compounds of formula I where $R_1$, $R_2$ and $R_4$ are hydrogen, and Ar is 1,4-naphthylene and n, $R_3$ and $R_5$ are as shown below.

| Molecular Weight | n | $R_3$ | $R_5$ |
|---|---|---|---|
| 681 | 1 | phenyl | phenyl substituted by the group A |
| 912 | 1 | phenyl-A | phenyl-A |
| 1143 | 2 | phenyl | phenyl-A |

A is a group of the formula

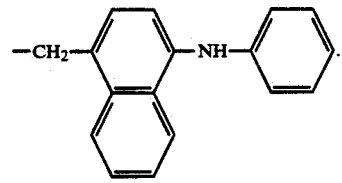

EXAMPLE 4

4,4'-Propylidene-bis[N-phenyl-1-naphthylamine]

The procedure of Example 1 is repeated using 43.9 g (0.2 mol) of N-phenyl-1-naphthylamine, 5.8 g (0.1 mol) of propionaldehyde and 1.5 mL of concentrated sulfuric acid in 250 mL of methanol to give 52 g of a dark oil. The residue is purified by chromatography to give 7.2 g (15% yield) of the title compound as a pink solid melting at 115° C.

Analysis

Calcd. for $C_{35}H_{30}N_2$: C, 87.8; H, 6.3; N, 5.8. Found: C, 87.4; H, 6.0; N 5.6.

EXAMPLE 5

The procedure of Example 1 is repeated using 21.93 g (0.1 mol) of N-phenyl-1-naphthylamine, 32.5 g (0.1 mol) of the reaction product of diphenylamine and 2,4,4- trimethylpentene [which contains N-(tert-octylphenyl-)aniline and N-(tert-butylphenyl)aniline as major components], 8.0 g (0.1 mol) of a 37.6% aqueous solution of formaldehyde and 2 mL of concentrated sulfuric acid in 300 mL of methanol to give 29 g of tan solid. Two components of the reaction product mixture are identified by mass spectroscopy.

(Octylanilino)phenylmethyl-N-phenyl-1-naphthylamine M/Z 512.

(Butylanilino)phenylmethyl-N-phenyl-1-naphthylamine M/Z 456.

EXAMPLE 6

4,4'-Methylene-bis[N-ethyl-1-naphthylamine]

The procedure of Example 1 is repeated using 34.3 g (0.2 mol) of N-ethyl-1-naphthylamine, 8.0 g (0.1 mol) of a 37.6% aqueous solution of formaldehyde and 1.8 mL of concentrated sulfuric acid in 250 mL of methanol to give a viscous reaction residue. The residue is triturated with 200 mL of hot isopropanol to give 29.6 g (83% yield) of the title compound as an off-white solid melting at 165°–168° C.

Analysis

Calcd. for $C_{25}H_{26}N_2$: C, 84.7; H, 7.4; N, 7.9. Found: C, 84.8; H, 7.5; N, 7.9.

EXAMPLE 7

High Temperature Stabilization of Lubricating Oil

The instant compounds of this invention are blended into a synthetic ester lubricating oil and tested in an oxidation test in accordance with the procedure described in Federal Test Method (FTM) Standard No. 791 C, Method No. 5308.7.

Thus, a 100 mL sample of the blended oil in contact with metal coupons of copper, magnesium, stainless steel, silver and aluminum is maintained at 400° F. for 72 hours while passing approximately 5 L per hour of air through the oil. After 72 hours, the corrosion of each metal (in milligrams weight loss), the acid number increase of the oil, the percent viscosity increase of the oil and the amount of sludge filtered from the oil (in milligrams per 100 mL of oil) are determined. The results are given in the tables below.

mentioned test. The additives of this invention are effective antioxidants as indicated by a smaller change in these two parameters relative to the untreated lubricant.

An additional objective of this invention is to provide a composition of additives which control the formation of sludge and inhibit the corrosion of metals as well as provide superior oxidation stability. A 1:1 mixture of the instant compounds of Examples 2, 3, or 5 with AO A provide such compositions.

Still another standard of performance for an aircraft turbine engine lubricating oil is meeting the requirements specified by the Naval Air Systems Command found in MIL-L-23699D, Apr. 2, 1990. The limits for corrosion and oxidation stability under this specification are: viscosity percent change = −5 to +25; total acid number, change max. = 3.0; metal weight change, mg/cm², max.:steel{St.} = ±0.2, silver(Ag) = ±0.2, aluminum(Al) = ±0.2, magnesium(Mg) = ±0.2, copper(Cu) = ±0.4; sludge content, filtered through 10 μm, mg/100 mL oil, max. = 50. The 1:1 mixtures sited previously and the compound of Example 1 meet or exceed these requirements.

EXAMPLE 8

Process Stabilization of Dynamically Crosslinked Polypropylene/Nitrile Rubber

To a Brabender Plasticorder heated to 190° C. is added 55 grams of dynamically crosslinked polypropylene/nitrile rubber (GEOLAST, Monsanto). The polymer is mixed under nitrogen for 3 minutes at 30 rpm and then 2.2 grams (4% by weight of the resin blend) of the test compound of Example 1 is added under nitrogen and mixed into the resin blend at 90 rpm for 7 minutes. The test sample is then removed from the Brabender and flattened in a cold press.

The test sample is then compression molded into plaques (4"×4"×60 mils; 10.16 cm×1.524 mm) at 200° C. for 4 minutes at 2000 psi (140 Kg/cm²) and then 4 minutes at 50,000 psi (3500 Kg/cm²).

The plaques are then cut into tensile bars and oven aged in a forced draft oven at 135° C. for 7 days.

The % elongation of triplicate bars are measured before and after oven aging. The greater the % retention of the % elongation, the more effective is the stabi-

| Additive* | Sludge (mg) | Viscosity (% Inc.) | Acid No. (Inc.) | Metals Corrosion (mg/cm²) | | | | |
|---|---|---|---|---|---|---|---|---|
| | | | | St. | Ag | Al | Mg | Cu |
| None | 22.6 | 104.95 | 6.09 | .007 | .007 | 0 | 20.4 | .04 |
| 2% Ex. 1 | 4.8 | 19.17 | 2.67 | 0 | .04 | .007 | .03 | .36 |
| 2% Ex. 2 | 156.4 | 13.11 | 1.77 | .09 | .06 | .08 | .14 | .14 |
| 2% Ex. 3 | 461.0 | 11.76 | 0.23 | .13 | .15 | .14 | .14 | .12 |
| 2% Ex. 4 | 1324 | 6.39 | 1.54 | .21 | .20 | .25 | .34 | .22 |
| 2% Ex. 6 | 1255 | 14.9 | 5.00 | 0 | .07 | .02 | .007 | .06 |
| 1% Ex. 2 + 1% AO A | 8.0 | 16.61 | 1.73 | .02 | .01 | 0 | .02 | .04 |
| 1% Ex. 3 + 1% AO A | 27.5 | 15.36 | 1.85 | .01 | .01 | .01 | .04 | 0 |
| 1% Ex. 4 + 1% AO A | 176.4 | 18.15 | 1.42 | .06 | .08 | .11 | .11 | .11 |
| 1% Ex. 6 + 1% AO A | 463.8 | 14.78 | 2.71 | 0.05 | 0.05 | 0.07 | 0.06 | 0.02 |
| None | 82.5 | 123.15 | 6.77 | 0.04 | 0.04 | .007 | 36.9 | 0.10 |
| 2% Ex. 5 | 129.9 | 6.14 | 0.94 | 0.12 | 0.08 | 0.12 | 0.11 | 0.14 |
| 1% Ex. 5 + 1% AO A | 14.9 | 14.14 | 1.25 | .007 | 0 | 0.03 | 0 | 0 |

*AO A is N,N-Di(4-tert-octylphenyl)amine

The primary measures of the antioxidant effectiveness of the instant compounds are the control of the acid number increase and the viscosity increase in the aforelizer compound.

| Stabilizer compound of | % Retention of % Elongation after 7 days at 135° C. |
|---|---|
| None | 11 |
| Example 1 | 32 |

What is claimed is:

1. A polymer composition stabilized against oxidative and thermal degradation which comprises
   (a) a polymer subject to thermal or oxidative degradation, and
   (b) an effective stabilizing amount of a compound of formula I

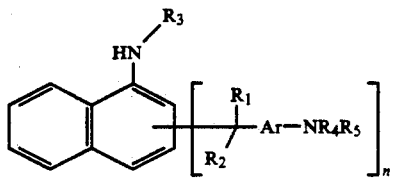

(I)

wherein
n is 1,
Ar is phenylene or naphthylene,
$R_1$ and $R_2$ are independently hydrogen, a straight or branched chain alkyl of 1 to 18 carbon atoms,
$R_3$ is an aryl group of 6 to 10 carbon substituted by one or two alkyl groups of 1 to 18 carbon atoms,
$R_4$ is hydrogen, and
$R_5$ is an aryl group of 6 to 10 carbon atoms substituted by one or two alkyl groups of 1 of 18 carbon atoms.

2. A composition according to claim 1 where in the compound of formula I,
$R_1$ is hydrogen,
$R_2$ is hydrogen or alkyl of 1 to 7 carbon atoms,
$R_3$ is phenyl substituted by one alkyl of 4 to 12 carbon atoms,
Ar is naphthylene,
$R_4$ is hydrogen, and
$R_5$ is phenyl substituted by one alkyl of 4 to 12 carbon atoms.

3. A composition according to claim 1 wherein the polymer is an elastomer.

4. A composition according to claim 3 wherein the elastomer is a dynamically crosslinked elastomer blend of a nitrile rubber with polypropylene.

5. A composition according to claim 1 wherein the compound of formula I is 4,4'-methylene-bis[N-(4-tert-octylphenyl)-1-naphthylamine].

6. A composition according to claim 1 wherein the compound of formula I is the condensation product mixture of N-(4-tert-octylphenyl)-1-naphthylamine and formaldehyde.

* * * * *